(12) United States Patent
Smith et al.

(10) Patent No.: US 12,419,827 B2
(45) Date of Patent: *Sep. 23, 2025

(54) NATURAL MOISTURIZER PRODUCTS

(71) Applicant: DVA INC., Vaughan (CA)

(72) Inventors: Gardiner F H Smith, Elizabeth, WV (US); Chia Chia Sun, Toronto (CA)

(73) Assignee: DVA INC., Vaughan (CA)

(*) Notice: Subject to any disclaimer, the term of this patent is extended or adjusted under 35 U.S.C. 154(b) by 0 days.

This patent is subject to a terminal disclaimer.

(21) Appl. No.: 18/143,528

(22) Filed: May 4, 2023

(65) Prior Publication Data

US 2023/0355503 A1 Nov. 9, 2023

Related U.S. Application Data

(63) Continuation of application No. 17/339,438, filed on Jun. 4, 2021, now Pat. No. 11,672,752.

(51) Int. Cl.
| | |
|---|---|
| *A61K 36/00* | (2006.01) |
| *A61K 8/34* | (2006.01) |
| *A61K 8/36* | (2006.01) |
| *A61K 8/60* | (2006.01) |
| *A61K 8/67* | (2006.01) |
| *A61K 8/73* | (2006.01) |
| *A61K 8/92* | (2006.01) |
| *A61K 8/9789* | (2017.01) |
| *A61Q 19/00* | (2006.01) |

(52) U.S. Cl.
CPC ............ *A61K 8/922* (2013.01); *A61K 8/347* (2013.01); *A61K 8/361* (2013.01); *A61K 8/604* (2013.01); *A61K 8/678* (2013.01); *A61K 8/735* (2013.01); *A61K 8/9789* (2017.08); *A61Q 19/005* (2013.01); *A61Q 19/007* (2013.01); *A61K 2800/30* (2013.01); *A61K 2800/5922* (2013.01)

(58) Field of Classification Search
CPC .......................... A61Q 19/005; A61Q 19/007
See application file for complete search history.

(56) References Cited

U.S. PATENT DOCUMENTS

| | | |
|---|---|---|
| 9,415,082 B1 | 8/2016 | Davis |
| 2009/0068128 A1 | 3/2009 | Constantine et al. |
| 2011/0250293 A1 | 10/2011 | Blomberg |
| 2015/0297501 A1 | 10/2015 | Constantine et al. |
| 2018/0049971 A1 | 2/2018 | Druilhet |
| 2021/0128443 A1 | 5/2021 | Smith et al. |
| 2021/0128450 A1 | 5/2021 | Smith et al. |

FOREIGN PATENT DOCUMENTS

| | | | | |
|---|---|---|---|---|
| CN | 105030584 B | * | 3/2018 | |
| DE | 102008039126 A1 | * | 2/2010 | ......... A61K 35/644 |
| WO | 2019/156923 A1 | | 8/2019 | |
| WO | 2020/086291 A1 | | 4/2020 | |
| WO | 2021/028655 A1 | | 2/2021 | |

OTHER PUBLICATIONS

Mitchell et al., "Efficacy of Vaginal Estradiol or Vaginal Moisturizer vs Placebo for Treating Postmenopausal Vuvlovaginal Symptoms a Randomized Clinical Trial", JAMA Intern Med., (2018), vol. 178, No. 5, pp. 681-690.

* cited by examiner

*Primary Examiner* — Qiuwen Mi
(74) *Attorney, Agent, or Firm* — Venable LLP; Keith G. Haddaway; Hemant Khanna

(57) ABSTRACT

The present invention is drawn to personal care products containing combinations of plant-based glyceride butters and plant-based glyceride oils, and their use in retaining moisture and natural flora in the skin, such as the hands and vaginal lips.

21 Claims, No Drawings

NATURAL MOISTURIZER PRODUCTS

REFERENCE TO EARLIER APPLICATIONS

This application is a continuation of U.S. application Ser. No. 17/339,438, filed Jun. 4, 2021, now allowed, the entire contents of which is incorporated herein by reference.

FIELD OF THE INVENTION

This invention relates to personal care products. More specifically, this invention relates to personal care products for use by women, especially those experiencing hormonal fluctuations or decline. Hormonal fluctuations or decline can be related to, for example, birth control, hormone therapy, menstruation, medications usage, childbirth, cancer treatment, polycystic ovary syndrome, perimenopause or menopause. The personal care products of the invention are for moisturizing skin and other body tissues, such as the hands or labia. In embodiments, the personal care products maintain and restore the tissue and skin's natural flora, moisturize the tissue and skin, and can provide soothing, topical relief and relaxation to tissue and skin.

BACKGROUND

Women's bodies undergo a myriad of changes through time, from puberty to childbearing years to post-menopause. Hormones in the body fluctuate during these time periods. Although hormonal changes occur throughout life, women experience the greatest hormonal changes during perimenopause and menopause. When a woman misses her period for 12 months consecutively, she has reached menopause. Perimenopause (menopausal transition) is the time period before a woman reaches menopause during which the female body is undergoing a transition in hormone production, and other biological functions related to childbearing and loss of fertility. Perimenopause can begin shortly after the prime childbearing years and occurs at a different age for each individual woman. While for most women, perimenopause begins in the 40s, for some, it can happen as early as the late 30s. The average age for women to reach menopause is about 52. Therefore, for some women, perimenopause can last 10 or more years. While many women are familiar with menopause and the biological changes that ensue, most have very little awareness of perimenopause and the changes associated with perimenopause. There is, thus, a continuing need for products that address biological changes of women that occur around and during this significant transition period.

During perimenopause, the production of estrogen, testosterone, and progesterone changes. As a result, women may experience symptoms such as: irregular periods, hot flashes, insomnia, night sweats, sleep irregularity, mood changes, vaginal dryness, vaginal pain, urinary urgency, discomfort during sex, fatigue, breast tenderness, low sex drive, and loss of bone density. However, not all women experience all the symptoms to the same degree.

A common problem occurring during perimenopause is tissue dryness. This dryness can occur in skin on any part of the body. However, dryness during perimenopause is a particular problem in delicate and sensitive tissues such as the breasts, the vulva, the vagina, the lips, and the face.

A particular underappreciated symptom of perimenopause is vulval dryness. The vulval includes the vaginal lips (labia majora and labia minora), clitoris, vulval vestibule, urinary meatus, vestibular glands, and the opening to the vagina. Vulval skin is more sensitive than skin on other parts of the body because it is much thinner. During perimenopause, women often experience vulval dryness, which causes symptoms such as itching, pain, rawness, and painful sex. Although commonly known to occur during menopause, many women are unaware that these are common problems prior to the onset of menopause, i.e. during perimenopause.

Another problem that frequently occurs in perimenopause and menopause is the onset of genitourinary syndrome and vaginal atrophy. Genitourinary syndrome, which relates to urgency, dysuria, and recurrent urinary tract infections, is associated with perimenopause and menopause. Vaginal atrophy (also known as atrophic vaginitis, vulvovaginal atrophy, or urogenital atrophy) is an inflammation of the vagina due to the thinning and shrinking of vaginal tissues, and decreased lubrication. Left unaddressed, vaginal atrophy can lead to pain and discomfort, including vaginal dryness, burning, and discharge; genital itching; burning or urgency with urination; discomfort during and light bleeding after intercourse; decreased vaginal lubrication during sexual activity; shortening and tightening of the vaginal canal; pelvic floor muscle seizure; and atrophy closure of the vagina including scarring and prolapse of an organ through the vagina. Sexual activity is essential to proper exercise, endogenous hormone maintenance, and maintenance of the vaginal track. When left untreated, vaginal dryness can result in painful micro-abrasions along the entire membrane of the vagina, shrinkage, scarring and closure.

Another specific problem during hormonal fluctuation is breast dryness or tenderness, also known as mastalgia. This can result in discomfort in normal daily activities, including disruption of normal movement, concentration, sleep, and intimacy.

Other specific problems associated with hormonal fluctuation are fatigue and/or lack of sleep. When the ovaries stop producing hormones at significant levels, the adrenal glands attempt to compensate. However, the adrenal glands only produce a small fraction of hormone that the ovaries produced prior to perimenopause and menopause. This reduction of hormone leads to fatigue. Exacerbating this problem is an adrenal response to the increased stress which fatigue can cause, where the adrenal glands consistently produce a rapid and large increase in cortisol. These cortisol spikes often occur in the middle of the night, interrupting sleep and preventing women from getting back to sleep. This condition of sleep interruption typically worsens over time if left unaddressed. Other associated symptoms may include confusion, increased moodiness, or mood changes.

Another generalized problem with hormonal fluctuation an increase in chemical hypersensitivity which accompanies dramatic hormonal decline. When the skin (in particular sensitive areas of the skin like the vaginal, vulva, labia, breasts, nipples, face, or lips) comes into contact with a cream or paste based product that contains synthetic chemicals, women experiencing perimenopause have a high potential to feel skin irritation, fatigue, and pain.

To alleviate some of the symptoms of hormonal fluctuation, women have been prescribed low-dose birth control pills to address the change of hormones in their bodies. Others have also used birth control skin patches, vaginal rings, and progesterone injections as hormone treatments. While replacement hormone therapy may alleviate some symptoms, such as hot flashes, sweats, and mood changes, it is less effective in treating dryness, such as skin dryness, breast dryness, vaginal dryness, and vulval dryness, as well as the concomitant results of dryness, including skin discomfort, breast sensitization, vaginal pain, and discomfort during sex. Women have also used personal lubricants, body lotions, and petroleum jelly-based products to ease some of these discomforts. However, neither topical hormone therapy nor use of chemical-laden moisturizer gels provides relief of the most bothersome symptoms of women over a 3-month period.

Unfortunately, alternatives such as personal lubricants, including water-based, synthetic oil-based, or silicone-based lubricants are undesirable because they contain synthetic chemicals, including preservatives and stabilizers. Thus, heightened chemical sensitivity in perimenopausal and menopausal women makes the use of chemical-based lubricants detrimental. Additionally, water and alcohol-based lubricants dehydrate the skin with medium- and long-term use, much like bathwater shrivels the skin on one's hands due to the concentration gradient across the skin membrane that pulls intracellular fluids out of the skin. Existing personal lubricants and moisturizers were designed to enhance the male experience with short term lack of friction during sexual activities, but in fact deteriorate the skin and mucous membrane of women. In a clinical trial by Mitchell et al. (JAMA Intern Med. 2018 May 1; 178(5):681-690), it was shown that neither a chemical-based moisturizer gel nor a topical vaginal hormone therapy were effective in improving symptoms over a 3 month period.

In their quest for natural product based solutions to these universal problems caused by normal aging of the female body, now representing a demographic of nearly half of all women, perimenopausal and menopausal women have attempted to use food type products, such as coconut oil or meat lard, as lubricants. The issue with the use of these products, besides not being produced under good manufacturing practices or being contaminant and pathogen tested, is that they do not promote a healthy pH in the vaginal and labial areas. During perimenopause, the vaginal tract goes from acidic to neutral, leading to conditions such as bacterial vaginosis, an infection where harmful bacteria replaces the normal healthy flora of a women's vaginal tract. In addition to the accompanying pain, odor and fever, these infections typically become chronic and marginally responsive to antibiotics. Women and health care providers often confuse and misdiagnose bacterial vaginosis infections with yeast infection, which typically occurs in women in conjunction with abnormal blood sugar levels. As a result of the misdiagnoses, women are being treated for yeast infections instead of bacterial vaginosis.

Therefore, there is a continuing unmet need for products that specifically target dryness, in particular dryness in sensitive areas, for women who are experiencing hormonal fluctuation. More importantly, an all-natural product is advantageous for the vulva to retain moisture while simultaneously avoiding irritation to the delicate mucous membrane of the vagina. Also, an all-natural product is preferable to bring the pH of a women's vaginal area to a healthy, acidic level such that the normal vaginal flora may be restored. A product that is free of alcohol and water is also highly desirable Furthermore, a product is needed to providing soothing, topical relief and relaxation to these sensitive areas for women experiencing hormonal fluctuations, particularly during perimenopause and menopause.

SUMMARY OF THE INVENTION

The following summary is presented for illustrative purposes and should not serve to limit the scope of the claimed subject matter.

One general aspect the invention includes a personal care product. The personal care product also includes a base of at least about 50 wt. % of at least one plant-based glyceride butter and at least about 15 wt. % of at least one plant-based glyceride oil. In another aspect, the personal care product includes from about 50 wt. % to about 85 wt. % of the at least one plant-based glyceride butter, and from about 15 wt. % to about 45 wt. % of the at least one plant-based oil. In another aspect, product includes from about 66 wt. % to about 72 wt. % of the at least one plant-based glyceride butter, and from about 24 wt. % to about 32 wt. % of the at least one plant-based oil.

In one aspect, the plant-based glyceride butter may include from about 15 wt. % to about 25 wt. % cocoa butter; from about 30 wt. % to about 45 wt. % shea nut butter; and from about 5 wt. % to about 15 wt. % kokum seed butter. In one aspect, the plant-based glyceride oil may include about 10 wt. % to about 20 wt. % high oleic sunflower seed oil; from about 2 wt. % to about 10 wt. % argan oil; from about 1 wt. % to about 5 wt. % borage oil; and from about 2 wt. % to about 10 wt. % apricot kernel oil.

In one aspect, the at least one plant-based glyceride butter may include from about 2.5 wt. % to about 3.9 wt. % linoleic acid; from about 20.9 wt. % to about 34.9 wt. % oleic acid; from about 5.3 wt. % to about 8.9 wt. % palmitic acid; and from about 20.4 wt. % to about 35.7 wt. % stearic acid. In one aspect, the at least one plant-based oil may include from about 2.3 wt. % to about 8.6 wt. % linoleic acid; from about 10.8 wt. % to about 29.4 wt. % oleic acid; from about 0.9 wt. % to about 3.1 wt. % palmitic acid; and from about 0.7 wt. % to about 2.1 wt. % stearic acid.

In one aspect, the plant-based glyceride butter may include from about 20 wt. % to about 22 wt. % cocoa butter; from about 37 wt. % to about 39 wt. % shea nut butter; and from about 9 wt. % to about 11 wt. % kokum seed butter. In one aspect, plant-based oil may include from about 12 wt. % to about 14 wt. % high oleic sunflower seed oil; from about 5 wt. % to about 7 wt. % argan oil; from about 2 wt. % to about 4 wt. % borage oil; and from about 5 wt. % to about 7 wt. % apricot kernel oil.

In one aspect, the at least one plant-based glyceride butter may include from about 3.2 wt. % to about 3.4 wt. % linoleic acid; from about 27.3 wt. % to about 29.6 wt. % oleic acid; from about 7.0 wt. % to about 7.7 wt. % palmitic acid; and from about 27.3 wt. % to about 29.9 wt. % stearic acid. In one aspect, the at least one plant-based oil may include from about 4.3 wt. % to about 6.2 wt. % linoleic acid; from about 16.3 wt. % to about 20.7 wt. % oleic acid; from about 1.6 wt. % to about 2.2 wt. % palmitic acid; and from about 1.1 wt. % to about 1.5 wt. % stearic acid.

The personal care product may further include one or more of: i) from about 0.005 wt. % to about 0.15 wt. % sodium hyaluronate; ii) from about 0.5 wt. % to about 1.5 wt. % sucrose cocoate; iii) from about 1.0 wt. % to about 5.0 wt. % vitamin E oil; and iv) from about 0.1 wt. % to about 0.5 wt. % sea buckthorn powder.

The personal care product may include: from about 0.5 mg/ml to about 1.5 mg/ml of cannabidiol (CBD) oil based on the total volume of the personal care product; and from about 10.0 mg/ml to about 15.0 mg/ml of CBD isolate based on the total volume of the personal care product.

The personal care product is substantially free of water and alcohol. The personal care product is substantially free of synthetic chemicals, synthetic anti-microbial agents, synthetic preservatives, or synthetic hormones.

The personal care product has a pH of from about 3.7 to about 6.5 in an aqueous environment. In some embodiments, the personal care product has a pH of from about 4.0 to about 5.5 in an aqueous environment. The personal care product can be in the form of a balm when stored at about 0° C. to about 5° C. for about 5 to about 10 minutes. The personal care product can be in the form of a serum when stored at about 36° C. to about 37° C. for about 1 to about 2 minutes.

One general aspect includes a method for manufacturing the personal care product. The method includes i) combining argan oil and high oleic sunflower oil together and heating the combination to an elevated temperature; ii) stirring into the combination cocoa butter, kokum seed butter, sucrose cocoate, and sodium hyaluronate to form a first mixture; iii) adding shea nut butter to the first mixture to form a second mixture: iv) adding to the second mixture borage oil, apricot kernel oil, and vitamin E oil, and heating the resulting formulation to an elevated temperature; v) stirring the formulation for a predetermined amount of time; vi) filtering the formulation; vii) filling the formulation into a product configuration; and viii) cooling the product configuration.

The method can further include stirring in CBD oil and CBD isolate together with the cocoa butter, kokum seed butter, sucrose cocoate, and sodium hyaluronate of step ii).

Another general aspect of the invention includes a method for maintaining and restoring the skin's natural flora and moisturizing the skin, including skin of the hands and vaginal lips. In one aspect, when administered topically the personal care product is effective for retaining moisture in the hands and retaining moisture and natural flora in the vaginal lips (labia majora and labia minora). Another aspect includes a method for treating skin irritation and soothing sensitive skin by applying onto the skin the personal care product.

DESCRIPTION OF EMBODIMENTS OF THE INVENTION

The present invention relates to a personal care product for alleviating skin dryness. In general, the personal care product promotes healthy skin and tissues. The personal care products can be used on anybody part of the body, such as the hands. The invention is particularly beneficial on skin in sensitive areas such as the labia (or vaginal lips), including both the labia majora and labia minora. In particular, the personal care product of the present invention is an all-natural product devoid of any artificial synthetic chemicals or synthetic hormones, and free of added alcohol or water. Embodiments of the present invention include a personal care product that contains at least 50 wt. % of at least one plant-based glyceride butter and at least 15 wt. % of at least one plant-based glyceride oil. The invention utilizes natural substances that provide an acidic pH when mixed in an aqueous environment or applied on the skin. These natural products and their lipophilicity and pH optimizing effect on sensitive skin and mucous membranes of women are novel and have benefits not achieved by existing products.

As used herein, the term "formulation" refers to the prepared personal care product and the terms are generally used interchangeably.

As used herein, the term "about" generally refers to the specific value, plus or minus 5% of said value.

As used herein, the term "balm" generally refers to an ointment or preparation used to heal or soothe the skin, and has a consistency somewhere between a heavy liquid and a solid. Balms are typically plant oil and wax-based and are thicker than lotions and creams, and do not contain water.

As used herein, the term "serum" generally refers to a skin care product designed to penetrate deeply into the skin to deliver targeted active ingredients that are quickly absorbed. Serums typically have a medium-body liquid consistency with a non-greasy finish.

All percentages refer to weight percent (wt. %) of the component in the final product, i.e. the weight of the component as compared to the total product weight, unless stated otherwise. Weight percentages are subject to precision and rounding and thus, in general, there is some variability in exact measures of weight percent, as would be readily recognized by persons skilled in the art.

As used herein, "plant glycerides" or "plant-based glycerides" refer to a plant extract of fatty acid glycerides that may include monoglycerides, diglycerides and triglycerides. In diglycerides and triglycerides, the fatty acids may be the same or different. Typical plant-based glycerides contain a mixture of glycerides with different fatty acids. However, the composition of glycerides from a particular plant extracted in a particular way provides a relatively consistent fatty acid content. Specific plant-based glycerides from various sources and in various forms are well known in the art.

As used herein, the term "plant-based glyceride butter" refers to a solid plant-based glyceride. As used herein, solid includes materials with semi-solid and cream-like consistency at room temperature, and thus includes materials frequently described as "pastes". Persons skilled in the art will readily recognize and identify what is meant by the terms "butter" and "paste" in this context, and as used herein the term "butter" includes "pastes" with their normal and accepted meanings.

As used herein, the term "plant-based glyceride oil" refers to a liquid plant-based glyceride. Typically, plant-based glyceride oils have a lower viscosity than water. Persons skilled in the art will readily recognize and identify what is meant by an "oil" in this context, and as used herein the term has its normal and accepted meaning.

As used herein, when a glyceride butter (or oil) is described as containing (or including or comprising) one or more fatty acids, it is to be understood that the fatty acids are not present as free fatty acids, but that the butter (or oil) contains glycerides that are composed of the identified fatty acids. Similarly, when glyceride butter or oil is described as containing a mixture of one or more fatty acids, it is to be understood that the mixture of fatty acids are not present as free fatty acids, but that the butter or oil contains glycerides that are composed of a mixture of the identified fatty acids. This does not imply that, for example, all triglycerides or a set of triglycerides all contain the same fatty acid, but that the butter (or oil) contains triglycerides in which at least one of the three fatty acids is the fatty acid recited. Further, there may be triglycerides that do not contain the specifically recited fatty acid. For example, a plant-based glyceride butter (or oil) containing stearic acid may include triglycerides that have 0-3 stearic acid moieties, but at least some contain at least one stearic acid moiety. Similarly, where the plant-based glyceride butter (or oil) is identified as containing a mixture of fatty acids, that mixture of fatty acids may be from a butter (or oil) extracted from a single source, or may be provided by a combination of butters (or oils) extracted from more than one source.

As will be appreciated, because the personal care product of the invention is non-aqueous, it does not have a readily quantifiable pH. Accordingly, references to pH in the present specification refer to the pH of the product in an aqueous environment. Because the skin contains some water, the pH described can be considered the pH obtained when the personal care product of the invention is applied to the skin.

An embodiment of the invention relates to a personal care product that may include natural ingredients, such as plant-based glycerides in the form of butters and oils, along with natural pharmaceutical and natural cosmetic ingredients. The natural pharmaceutical and natural cosmetic ingredients include, for example, vitamin E oil, sodium hyaluronate, sucrose cocoate, sea buckthorn powder, cannabinoids such as cannabidiol, and plant extracts containing these ingredients. Other active pharmaceutical or cosmetic ingredients compatible with the personal care products of the invention include, for example, melatonin, retinoic acid, vitamin C, collagen, glycolic acid, salicylic acid, squalene, caffeine, and other natural ingredients.

As used herein, the term hyaluronic acid refers not only to the acid, but also to salts such as sodium hyaluronate, and the terms are used interchangeably. Unless specified otherwise, sodium hyaluronate can be replaced with other hyaluronic acid salts such as potassium hyaluronate and the like. In general, hyaluronic acid and hyaluronate salts can be used interchangeably in products and formulations of the invention, unless stated otherwise. Persons skilled in the art will be able to identify appropriate forms of hyaluronic acid. The hyaluronic acid used in the present invention can be obtained from a natural source or a synthetic bioidentical hyaluronic acid that is indistinguishable from naturally occurring hyaluronic acid.

As used herein and unless identified otherwise or otherwise clear from context, the term "cannabis oil" generally refers to a hemp extract containing one or more cannabinoids, as identified herein, or cannabinoids that may be obtained from a hemp extract. The cannabis oil may contain a particular cannabinoid compound, a class of structurally related cannabinoid compounds, or a range of cannabinoid compounds. As such, a cannabis oil may comprise a single compound or a mixture of compounds. Cannabis oil can also be a mixture of cannabinoids from any source. Cannabinoids used in the present invention can be obtained from a natural source or can be a synthetic bioidentical cannabinoid that is indistinguishable from a naturally occurring cannabinoid.

Plant-based glycerides are extracted from plants. Plant-based glycerides can include a variety of saturated and unsaturated fatty acids including, for example, palmitic acid, stearic acid, linoleic acid, linolenic acid, arachidic acid, oleic acid, and others, esterified onto glycerol to form the glycerides. The plant-based glycerides are in the form of a butter or (solid at room temperature) or paste (semi-solid or cream-like at room temperature), or an oil (liquid at room temperature). The physical properties depend on the specific composition of the glycerides (mono-, di-, or triglycerides) and the fatty acid composition of the glycerides. Most plant-based glycerides are triglycerides and, accordingly, the physical properties depend on the fatty acid composition. Examples of plant-based glycerides include extracts of shea, cocoa, kokum, mango, palm, sunflower, argan, borage, walnut, avocado, apricot, and almond, many of which may be in the form of a butter (or paste), or oil. Other plants may be used to obtain plant-based glycerides. These products are well-known and have their generally accepted meaning as understood in the art. In some embodiments, the plant-based glycerides are deodorized.

While the present invention has been described as containing cocoa butter, kokum butter and shea nut butter, it will be appreciated that one or more of these specific plant-based glyceride butters may be replaced by a plant-based glyceride butter of different origin, i.e. from a different plant. If a different plant-based glyceride butter is used in place of a single recited butter, it should have similar physical properties to the butter it replaces; in particular, similar consistency and behavior, and preferably also contain a similar distribution of fatty acids, to provide properties consistent with the teachings of this specification. If a different mixture of plant-based glyceride butters is used in place of the recited mixture of butters, the mixture should have similar physical properties to the claimed mixture it replaces; in particular, similar consistency and behavior, and preferably also contain a similar distribution of fatty acids, to provide properties consistent with the teachings of this specification.

Likewise, while the present invention has been described as containing high oleic sunflower seed oil, argan oil, borage oil, and apricot kernel oil, it will be appreciated that one or more of these specific plant-based glyceride oils may be replaced by a plant-based glyceride oil of different origin. If a different plant-based glyceride oil is used in place of a single recited oil, it should have similar physical properties to the oil it replaces; in particular, similar consistency and behavior, and preferably also contain a similar distribution of fatty acids, to provide properties consistent with the teachings of this specification. If a different mixture of plant-based glyceride oils is used in place of the recited mixture of oils, the mixture should have similar physical properties to the claimed mixture it replaces; in particular, similar consistency and behavior, and preferably also contain a similar distribution of fatty acids, to provide properties consistent with the teachings Embodiments of the invention may include cocoa butter, an edible vegetable fat extracted from the cocoa bean. Cocoa butter has a cocoa flavor and aroma. Its melting point is just below human body temperature. Cocoa butter contains between 57-64% saturated fats and 36-43% unsaturated fats. Cocoa butter typically contains about 3.2% linoleic acid, about 34.5% oleic acid, about 26.0% palmitic acid, and about 34.5% stearic acid. Embodiments of the invention include from about 15 wt. % to about 25 wt. % cocoa butter, or preferably from about 20 wt. % to about 22 wt. % cocoa butter. In another preferred embodiment, the invention includes about 20.5 wt. % cocoa butter.

Embodiments of the invention may include shea nut butter, also referred to at times as shea olein. Shea nut butter is an off-white or ivory-colored natural glyceride extracted from the nuts of shea trees. Shea nut butter melts at body temperature and it is absorbed rapidly into the skin. Shea nut butter typically contains about 6.6% linoleic acid, about 46.4% oleic acid, about 4.0% palmitic acid, and about 41.5% stearic acid. Embodiments of the invention include from about 30 wt. % to about 45 wt. % shea nut butter, or preferably from about 37 wt. % to about 39 wt. % shea nut butter. In another preferred embodiment, the invention includes about 38.0 wt. % shea nut butter.

Embodiments of the invention may include kokum butter. Kokum butter is extracted from the seeds of the kokum tree. Kokum butter contains up to 60-65% saturated fatty acid and is a solid at room temperature. Kokum butter typically contains about 1.0% linoleic acid, about 36.0% oleic acid, about 4.0% palmitic acid, and about 56.0% stearic acid. Embodiments of the invention include from about 5 wt. % to about 15 wt. % kokum butter, or preferably from about 9 wt. % to about 11 wt. % kokum butter. In another preferred embodiment, the invention includes about 10.0 wt. % kokum butter. In embodiments of the invention, the kokum butter may be deodorized.

Embodiments of the invention may include sunflower seed oil. Sunflower seed oil is a source of glycerides of palmitic acid, stearic acid, oleic acid, and linoleic acid. Four types of sunflower seed oils exist, each with varying concentrations of said glycerides, any of which may be used alone or in combination in the personal care products of the invention. The four types of sunflower seed oils are i) high-linoleic which contains about 69% linoleic acid; ii) high-oleic which contains about 82% oleic acid; iii) mid-oleic which contains about 65% oleic acid; and iv) high-stearic high-oleic which contains about 18% stearic acid and 72% oleic acid. Preferably, high-oleic sunflower seed oil is used in embodiments of the invention. High-oleic sunflower seed oil typically contains about 9.0% linoleic acid, about 82.0% oleic acid, about 4.0% palmitic acid, and about 5.0% stearic acid. Embodiments of the invention include about 10 wt. % to about 20 wt. % high oleic sunflower seed oil, or preferably about 12 wt. % to about 14 wt. % high oleic sunflower seed oil. In another preferred embodiment, the invention includes about 13.1 wt. % high oleic sunflower seed oil.

Embodiments of the invention may include argan oil. Argan oil is derived from the kernels of the argan tree. Argan oil contains mostly fatty acids, including oleic acid, linoleic acid, palmitic acid, and linolenic acid. Argan oil typically contains about 32.5% linoleic acid, about 46.0% oleic acid, about 13.0% palmitic acid, and about 5.5% stearic acid. Embodiments of the invention include about 2 wt. % to about 10 wt. % argan oil, or preferably about 5 wt. % to about 7 wt. % argan oil. In another preferred embodiment, the invention includes about 6.0 wt. % argan oil.

Embodiments of the invention may include borage oil. Borage oil is derived from the seeds of the *Borago officinalis*. Borage oil has one of the highest amounts of Y-linolenic acid (GLA) of seed oils. Borage oil typically contains about 36.6% linoleic acid, about 18.5% oleic acid, about 10.7% palmitic acid, and about 6.4% stearic acid. Embodiments of the invention include about 1 wt. % to about 5 wt. % borage oil, or preferably about 2 wt. % to about 4 wt. % borage oil. In another preferred embodiment, the invention includes about 3.0 wt. % borage oil.

Embodiments of the invention may include apricot kernel oil. Apricot kernel oil (or Apricot oil) is derived from the kernels of the *Prunus armeniaca*. Apricot kernel oil contains mostly oleic and linoleic acid, as well as vitamin A, vitamin E, omega 9, omega 6, omega 4, palmitic acid, and stearic acid. Apricot kernel oil typically contains about 17.5% linoleic acid, about 75.0% oleic acid, about 10.7% palmitic acid, and about 6.4% stearic acid. Embodiments of the invention include about 2 wt. % to about 10 wt. % apricot kernel oil, or preferably about 5 wt. % to about 7 wt. % apricot kernel oil. In another preferred embodiment, the invention includes about 6.0 wt. % borage oil or about 6.4 wt. % apricot kernel oil.

Embodiments of the invention include at least one plant-based glyceride as a base material containing at least one plant-based glyceride butter and at least one plant-based glyceride oil. For example, in embodiments of the invention, the base material may include cocoa butter, kokum butter, shea nut butter, high-oleic sunflower seed oil, argan oil, borage oil, and apricot kernel oil. The selection and amounts of plant-based glycerides can be varied to achieve desired physical properties. The identity and quantities of materials described herein give particularly desirable physical characteristics. In exemplary embodiments, the desired physical properties and characteristics are obtained by providing one or more plant-based glyceride butters that, in combination, have a fatty acid content as identified herein or that have a fatty acid content is similar to that obtained from the combination of plant-based glyceride butters identified herein, in combination with one or more plant-based glyceride oils that, in combination, have a fatty acid content as identified herein or that have a fatty acid content is similar to that obtained from the combination of plant-based glyceride oils identified herein.

Embodiments of the invention include a plant-based glyceride base which contains at least 50 wt. % of the at least one plant-based glyceride butter and at least 15 wt. % of the at least one plant-based glyceride oil. As used herein, "at least 50 wt. % of the at least one plant-based glyceride butter" and similar expressions means at least 50 wt. % total plant-based glyceride butter, which may be made up of one or more plant-based glyceride butters. In a preferred embodiment, the plant-based glyceride base contains about 50 wt. % to about 85 wt. % of the at least one plant-based glyceride butter and from about 15 wt. % to about 45 wt. % of the at least one plant-based glyceride oil. In another preferred embodiment, the plant-based glyceride base contains from about 68 wt. % to about 72 wt. % of at least one plant-based glyceride butter and from about 24 wt. % to about 32 wt. % of at least one plant-based glyceride oil.

Embodiments of the invention include a plant-based glyceride butter containing cocoa butter, shea nut butter, and kokum seed butter. Embodiments of the invention include a plant-based glyceride butter containing from about 15 wt. % to about 25 wt. % cocoa butter, from about 30 wt. % to about 45 wt. % shea nut butter, and from about 5 wt. % to about 15 wt. % kokum seed butter. In a preferred embodiment, the plant-based glyceride butter contains from about 20 wt. % to about 22 wt. % cocoa butter, from about 37 wt. % to about 39 wt. % shea nut butter, and from about 9 wt. % to about 11 wt. % kokum seed butter.

Embodiments of the invention include a plant-based glyceride butter component containing from about 2.5 wt. % to about 3.9 wt. % linoleic acid, from about 20.9 wt. % to about 34.9 wt. % oleic acid, from about 5.3 wt. % to about 8.9 wt. % palmitic acid, and from about 20.4 wt. % to about 35.7 wt. % stearic acid. In a preferred embodiment, of the plant-based glyceride butter component contains from about 3.2 wt. % to about 3.4 wt. % linoleic acid, from about 27.3 wt. % to about 29.6 wt. % oleic acid, from about 7.0 wt. % to about 7.7 wt. % palmitic acid, and from about 27.3 wt. % to about 29.9 wt. % stearic acid.

Embodiments of the invention include a plant-based glyceride oil containing high-oleic sunflower seed oil, argan oil, borage oil, and apricot kernel oil. Embodiments of the invention include a plant-based glyceride oil containing from about 10 wt. % to about 20 wt. % high-oleic sunflower seed oil, from about 2 wt. % to about 10 wt. % argan oil, from about 1 wt. % to about 5 wt. % borage oil, and from about 2 wt. % to about 10 wt. % apricot kernel oil. In a preferred embodiment, the plant-based glyceride oil contains from about 12 wt. % to about 14 wt. % sunflower seed oil, from about 5 wt. % to about 7 wt. % argan oil, from about 2 wt. % to about 4 wt. % borage oil, and from about 5 wt. % to about 7 wt. % apricot kernel oil.

Embodiments of the invention include at least one plant-based glyceride oil component containing from about 2.3 wt. % to about 8.6 wt. % linoleic acid, from about 10.8 wt. % to about 29.4 wt. % oleic acid, from about 0.9 wt. % to about 3.1 wt. % palmitic acid, and from about 0.7 wt. % to about 2.1 wt. % stearic acid. In a preferred embodiment, the at least one plant-based glyceride oil contains from about 4.3 wt. % to about 6.2 wt. % linoleic acid, from about 16.3 wt. % to about 20.7 wt. % oleic acid, from about 1.6 wt. % to about 2.2 wt. % palmitic acid; and from about 1.1 wt. % to about 1.5 wt. % stearic acid.

According to the invention, the combination of at least one plant-based glyceride butter and at least one plant-based glyceride oil is selected to achieve a base consistency that, depending on the temperature and duration at which the product configuration is stored, the personal care product contained therein achieves the consistency of a balm or that of a serum. At room temperature (i.e. about 20° C. to about 22° C.) the product has the consistency of a cream. At about 15° C. to about 16° C. and below the product is a balm. At temperatures of about 30° C. and above the product is a serum. To obtain a balm consistency the product configuration is stored at about 0° C. to about 5° C., such as in a freezer or refrigerator, for about 5 to about 10 minutes. To obtain a serum consistency, the product configuration is stored at about 36° C. to about 37° C., such as by holding the product configuration in an individual's hands, for about 1 to about 2 minutes.

The product of the invention performs well at temperatures between 50° F. and 95° F. (10° C. to 35° C.). The present invention provides a stable and consistent formulation. The product of the invention is stable when cycled through multiple melt/freeze cycles, for example by being frozen and melted three times. The product is similarly stable based on multiple year stability testing using, for example, industry standard accelerated stability testing. Stability is measured based on consistency of physical properties, for example, it remains homogeneous through various temperatures and upon storage and returning to or maintains its original viscosity and transdermal transport properties. The product also maintains a variation of less than 5% with respect to any ingredient result upon stability or temperature testing. Variations of greater than 5% result in reduced product performance.

Water and alcohols are dehydrating to skin membranes due to the concentration gradient of salts and sugars in intracellular fluids. Embodiments of the invention relate to a personal care product that is substantially free of added water or alcohols, including diols and polyols. For example, substantially free can mean that the personal care product has less than about 5 wt. % of added water or alcohols, less than about 4 wt. % of added water or alcohols, less than about 3 wt. % of added water or alcohols, less than about 2 wt. % of added water or alcohols, less than about 1 wt. % added water or alcohols, less than about 0.5 wt. % added water or alcohols, less than about 0.1 wt. % added water or alcohols, or less than about 0.05 wt. % added water or alcohols. For example, the personal care product is substantially free of methanol, ethanol, propanol, and other monohydric alcohols; ethylene glycol, propylene glycol, and other diols; and glycerol (glycerin), and other polyols. In exemplary embodiments, the personal care product is substantially free of added water or alcohols. In exemplary embodiments, the personal care product contains no added water or alcohols, although residual water or alcohol in one of the components added to the product may be present.

Embodiments of the invention relate to personal care products that are substantially free of synthetic chemicals, such as synthetic preservatives, anti-microbial agents, or chemical stabilizers. Synthetic chemicals exclude materials that are synthesized and indistinguishable from the corresponding bio-generated or natural material in all respects. In other words, synthetic bio-identical materials are not considered to be synthetic chemicals. Examples of synthetic preservatives, antimicrobial agents, and chemical stabilizers include benzoates (e.g., benzoic acid and sodium benzoate), hydroxybenzoate and derivatives, sorbates (e.g., sorbic acid and sodium sorbate), propionates, nitrates, nitrites, sulfites (sulfur dioxide, sodium bisulfite), chelating agents, propyl gallate, gallic acid, sodium gallate, methyl paraben, propyl paraben, butyl paraben, ethyl paraben, quaternium-15, formaldehyde, lactic acid, propionic acid, sodium propionate, ascorbic acid, sodium ascorbate, butylated hydroxytoluene, butylated hydroxyanisole, and synthetic tocopherols. For example, the personal care product has less than about 5 wt. % of added synthetic chemicals, less than about 4 wt. % added synthetic chemicals, less than about 3 wt. % added synthetic chemicals, less than about 2 wt. % of added synthetic chemicals, less than about 1 wt. % added synthetic chemicals, less than about 0.5 wt. % added synthetic chemicals, less than about 0.1 wt. % added synthetic chemicals, or less than about 0.05 wt. % added synthetic chemicals. A particular advantage of the present invention is that it avoids the use of synthetic preservatives generally necessary for aqueous formulations. For example, the personal care product has less than about 5 wt. % of added synthetic preservatives or anti-microbial agents, less than about 4 wt. % added synthetic preservatives or anti-microbial agents, less than about 3 wt. % added synthetic preservatives or anti-microbial agents, less than about 2 wt. % of added synthetic preservatives or anti-microbial agents, less than about 1 wt. % added synthetic preservatives or anti-microbial agents, less than about 0.5 wt. % added synthetic preservatives or anti-microbial agents, less than about 0.1 wt. % added synthetic preservatives or anti-microbial agents, or less than about 0.05 wt. % added synthetic preservatives or anti-microbial agents. For example, the personal care product has less than about 5 wt. % of added chemical stabilizers, less than about 4 wt. % added chemical stabilizers, less than about 3 wt. % added chemical stabilizers, less than about 2 wt. % of added chemical stabilizers, less than about 1 wt. % added chemical stabilizers, less than about 0.5 wt. % added chemical stabilizers, less than about 0.1 wt. % added chemical stabilizers, or less than about 0.05 wt. % added chemical stabilizers. In exemplary embodiments, the personal care product is substantially free of added synthetic chemicals, such as synthetic preservatives, anti-microbial agents, or chemical stabilizers. In exemplary embodiments, the personal care product contains no added synthetic chemicals, such as synthetic preservatives, anti-microbial agents, or chemical stabilizers.

Embodiments of the invention include sucrose cocoate. Sucrose cocoate is a mild surfactant and emulsifier. Sucrose cocoate is prepared from a blend of coconut oil, fatty acids, and sucrose esters derived from plants, such as sugar beets. Embodiments of the invention include from about 0.5 wt. % to about 1.5 wt. % sucrose cocoate. In a preferred embodiment, the invention includes about 1.0 wt. % sucrose cocoate.

Embodiments of the invention include Vitamin E. Vitamin E is a natural preservative which protects lipids and prevents the oxidation of polyunsaturated fatty acids. Embodiments of the invention include about 0.1 wt. % to about 10 wt. % Vitamin E, about 1 wt. % to about 5 wt. % Vitamin E, or about 1 wt. % to about 3 wt. % Vitamin E. In an exemplary embodiment, the invention includes about 2.0 wt. % Vitamin E. Other natural preservatives may also be used.

Hyaluronic acid is a non-sulfated glycosaminoglycan, naturally found in the body and is the main component of the extra cellular matrix. Hyaluronic acid is found in high levels in the skin, where it is naturally produced by both fibroblasts and keratinocytes and exists as a polymer of medium molecular weight (600-1,000 kDa). An important function of hyaluronic acid is to hold water in the intercellular matrix of the connective tissue. This water-binding capacity significantly contributes to the elasticity of the skin, serving as a water reservoir. With aging, the quantity and quality of hyaluronic acid in the skin decreases, leading to skin dryness.

Embodiments of the invention may include hyaluronic acid or its derivatives. Hyaluronic acid is a skin hydrating agent that can help restore water to dehydrated skin. When applied according to a method of the invention, hyaluronic acid molecules can deliver substantially instant hydration to the skin. As used herein, the term hyaluronic acid refers not only to the acid, but also to salts such as sodium hyaluronate. Similarly, unless specified otherwise, sodium hyaluronate can be replaced with other hyaluronic acid salts such as potassium hyaluronate and the like. In general, hyaluronic acid and hyaluronate salts can be used interchangeably in products and formulations of the invention, unless stated otherwise. Persons skilled in the art will be able to identify appropriate forms of hyaluronic acid.

The hyaluronic acid used in the invention generally has a very low molecular weight, e.g. about 100 kDa or less, about 50 kDa or less, or about 5 kDa. This low molecular weight allows for increased permeation through the skin compared to high molecular weight hyaluronic acid. The hyaluronic acid can rejuvenate the skin by improving its viscoelastic properties and significantly decreases deep wrinkles. Hyaluronic acid is commercially available from a number of sources. Embodiments of the invention include about 0.0005 wt. % to about 0.050 wt. % hyaluronic acid, about 0.001 wt. % to about 0.025 wt. % hyaluronic acid, or preferably about 0.005 wt. % to about 0.015 wt. % hyaluronic acid. In another preferred embodiment, the invention includes about 0.010% hyaluronic acid.

Embodiments of the invention may include sea buckthorn powder or an extract of sea buckthorn (*Hippophae rhamnoides*). In some embodiments, sea buckthorn oil extracted from sea buckthorn berries may be used. Sea buckthorn oil is believed to be a skin softener or moisturizer. Furthermore, sea buckthorn powder contains omega-7 fatty acids and when dissolved in a mixture, it generates an acidic pH in the mixture. The acidic nature of the sea buckthorn may restore the pH level of the vaginal area to a pH of 3.5 to 4.5, for example around 3.7, thus creating an environment where the vaginal flora may be restored. When present, embodiments of the invention include from 0.005 wt. % to about 1.5 wt. % sea buckthorn powder, about 0.010 wt. % to about 1.0 wt. % sea buckthorn powder, or about 0.05 wt. % to about 0.5 wt. %. Some embodiments of the invention preferably include about 0.1 wt. % sea buckthorn powder or extract. In other preferred embodiments, sea buckthorn powder or extract is not present.

Embodiments of the invention can include cannabinoids. Cannabinoids have been the subject of a great deal of recent research and have many benefits on physical and mental health. Cannabinoids are compounds isolated from (or synthetic compounds identical to compounds isolated from) cannabis and other related plants. Cannabinoids useful in the invention include extracts that are a mixture of cannabinoids, enhanced or enriched extracts containing an enhanced amount of a particular cannabinoid, such as cannabidiol, or group of cannabinoids, or extracts and isolates containing only a single cannabinoid. For example, one or more cannabinoid compounds can be individually isolated or synthesized for use in the composition. Exemplary cannabinoids include THCA (Tetrahydrocannabinolic acid), CBD (Cannabidiol), CBDA (Cannabidiolic Acid), CBN (Cannabinol), CBG (Cannabigerol), CBC (Cannabichromene), CBL (Cannabicyclol), CBV (Cannabivarin), THCV (Tetrahydrocannabivarin), CBDV (Cannabidivarin), CBCV (Cannabichromevarin), CBGV (Cannabigerovarin), CBGM (Cannabigerol Monomethyl Ether), CBE (Cannabielsoin), and CBT (Cannabicitran).

Cannabinoids used in the invention can come from hemp oil. Hemp oil is an extract of the hemp plant, typically an industrial hemp plant, and contains terpenes and other cannabinoids. Because it is from the hemp plant, broad-spectrum Hemp oil contains little or no THC, and always less than 3% THC.

Embodiments of the invention may include CBD. CBD may be added in several forms, alone or in combination. Suitable sources of CBD include CBD isolate, and CBD oil. CBD isolate is the purest form of CBD, obtained by refining CBD oil and can be an oil, solid, or crystalline product. As used herein, CBD oil is a cannabis oil that predominately contains CBD. Embodiments of the invention may include a CBD isolate such that the final concentration of CBD isolate in the personal care product is from about 10 mg/mL to about 15 mg/mL CBD isolate, i.e. about 1.0% to about 1.5% CBD isolate. In a preferred embodiment, the invention includes about 12.5 mg/mL of CBD isolate, i.e. about 1.0% to about 1.5% CBD isolate.

CBD oil is a cannabis oil that predominately contains CBD. CBD oil is an extract of the cannabis plant (i.e. a hemp extract) containing other compounds, such as terpenes and other cannabinoids, but which has undergone a refinement process such as distillation and/or extraction to enhance the CBD content. CBD oil may contain greater than 60% CBD, greater than 65% CBD, greater than 70% CBD, for example, from about 60% to about 90% CBD, from about 70% to about 80% CBD, or about 70 to about 75% CBD. Because it is from the cannabis plant, CBD oil may contain up to 3% THC. Embodiments of the invention may include CBD oil such that the final concentration of CBD oil in the personal care product is from about 0.5 mg/mL to about 1.5 mg/mL, i.e. about 0.05% to about 0.15% CBD oil.

In some embodiments, the cannabinoid containing component, e.g., CBD or hemp oil, is refined so that it lacks any detectable cannabis odor. In some embodiments, the CBD or hemp oil is refined so that it lacks any detectable cannabis terpenes. Extracts lacking cannabis odor and/or terpenes are particularly desirable for use in cosmetic products.

Another embodiment of the invention relates to a personal care product that may be used to alleviate vulval dryness, specifically dryness of vaginal lips, including the labia majora and labia minora.

Another embodiment of the invention relates to a personal care product that may be used to alleviate dry hands or wrinkled, crepey skin. In embodiments of the invention, the personal care product smooths or improves the appearance of wrinkled and crepey skin The combination of ingredients, in particular the combination of at least one plant-based glyceride butters and hyaluronic acid, are selected to achieve an optimal pH for the particular application. When mixed with an aqueous environment, personal care compositions of the invention can have a pH ranging from about 3.7 to about 6.5. When the pH of the vaginal tract shifts from acidic to neutral during perimenopause and menopause, it allows pathogenic bacteria to replace the natural flora, resulting in recurring infections such as bacterial vaginosis. Returning the pH to pre-menopausal acidic levels on the surface of the vaginal tract can promote healthy bacterial flora and reduce bacterial vaginosis.

In an embodiment, a formulation for alleviating dryness, for example skin, vulval or labial dryness, may include natural ingredients, such as, at least 50 wt. % of at least one plant-based glyceride butter; and at least 15 wt. % of at least one plant-based glyceride oil. In an embodiment, a formulation for alleviating dryness may include natural ingredients, such as, from about 50 wt. % to about 85 wt. % of at least one plant-based glyceride butter; from about 15 wt. % to about 45 wt. % of at least one plant-based glyceride oil; and from about 0.005 to about 0.015 wt. % sodium hyaluronate. In an embodiment, a formulation for alleviating dryness may include natural ingredients, such as, from about 66 wt. % to about 72 wt. % of at least one plant-based glyceride butter; from about 24 wt. % to about 32 wt. % of at least one plant-based glyceride oil; and from about 0.005 to about 0.015 wt. % sodium hyaluronate.

Embodiments of the invention relate to a method for restoring the skin's natural flora and moisturizing the skin by topically applying the personal care product by, for example, retaining moisture. The personal care product of the invention is particularly effective for retaining moisture in vaginal lips. In embodiments of the invention, the personal care product is effective for retaining moisture and natural flora in the skin and vaginal lips, including the labia majora and labia minora. In embodiments of the invention, the personal care product is topically applied to the skin as a serum. In embodiments of the invention, the personal care product is topically applied to the skin as a balm.

Embodiments of the invention relate to a method for treating skin irritation and soothing sensitive skin by topically applying the personal care product. In embodiments of the invention, the skin irritation can be due to dryness or itching. Soothing of skin can be evaluated by reduction of pain, reduction of hypersensitivity, or reduction of irregular skin texture.

The present invention can promote efficacy in treating symptoms of vaginal dryness, prevent stenosis when used in combination with a dilator, and prevent dryness associated with using an alcohol-based gel. The invention can be used in advance of intercourse, with a dilator and/or for general vaginal comfort. Clinical trials indicate that women who use labial moisturizers benefit from decreased vaginal discomfort, improvements in intercourse comfort and enjoyment, and increased vaginal health and well-being.

Cancer of the vulva, vagina, uterine cervix and uterine corpus is routinely treated with external beam radiation and brachytherapy. Treatment methods often cause short-term inflammation, bleeding, soreness and irritation and long-term vaginal scarring and stenosis (narrowing). In extreme cases, the vaginal wall can fuse together and scar shut. Cancer patients are counselled to utilize a dilator (glass, plastic or rubber) to prevent the vaginal wall from becoming narrower and shorter. The vaginal tissue also becomes drier and less elastic, particularly if pelvic radiation has damaged the ovaries and induced menopause. The benefits of the invention are useful in alleviating difficulties associated with pelvic radiation treatments.

Embodiments of the invention relate to a method for manufacturing a personal care formulation. The method includes the steps of:
i) Combining aragan oil and high oleic sunflower oil and heating the combination at an elevated temperature;
ii) Stirring into to the combination cocoa butter, kokum seed butter, sucrose cocoate, and sodium hyaluronate to form a first mixture;
iii) Adding shea nut butter to the first mixture to form a second mixture;
iv) Adding borage oil, apricot kernel oil, and vitamin E oil to the second mixture;
v) Stirring the formulation for a predetermined amount of time;
vi) Filtering the formulation;
vii) Filling the formulation into the product configuration;
viii) Cooling the product configuration to 4° C.

Embodiments of the invention can include the addition of any one of sea buckthorn powder/extract, CBD oil, and CBD in step ii).

In embodiments of the invention, the elevated temperature of steps i) and step iv) is about 65° C. In embodiments of the invention, the elevated temperature is maintained from step i)-step vii). In embodiments of the invention, the predetermined stirring time in step v) is about 45 minutes. In embodiments of the invention, the formulation is cooled quickly after placement in the product configuration.

Embodiments of the invention relate to using pharmaceutical grade ingredients, manufacturing under good manufacturing practice, and testing final product for levels of heavy metals below 0.1 ppm, yeast and mold less than 10 cfu/g, and negative detection for *E. Coli, salmonella, Staphylococcus aureus* and *Pseudomonas aeruginosa*.

Products according to the present invention are stable. For example, the personal care products can be subjected to multiple freezing and melting cycles. This process involves heating the product configuration to about 24° C. such that the product melts, followed by cooling the product to 4° C. such that the product freezes. The product configuration is cycled through this temperature range several times to repeatedly melt and freeze the personal care product and then evaluated. Product properties remain consistent throughout the process. In addition, the CBD containing personal care products are stable in that the CBD content varies by less than 15% year-to-year.

Embodiments of the invention are described by the following non-limiting examples.

EXAMPLES

Example 1—General Base Formulas

A general base formula for the personal care products of the present invention is disclosed in Table 1A below. Exemplary formulation A serves as the base for hand moisturizers of the present invention. Exemplary formulation B serves as the base for labial moisturizers of the present invention.

TABLE 1A

| Ingredient | Possible Range (wt. %) | Exemplary Range (wt. %) | Exemplary Formulation A | Exemplary Formulation B |
| --- | --- | --- | --- | --- |
| *Theobroma cacao* (cocoa) butter | 15.0-25.0 | 20.0-22.0 | 0.627 g | 0.612 g |
| *Butyrosperum parkii* (shea nut) butter | 30.0-45.0 | 37.0-39.0 | 1.14 g | 1.14 g |
| *Garcinia indica* (kokum) seed butter | 5.0-15.0 | 9.0-11.0 | 0.3 g | 0.3 g |
| *Helianthus annuus* (sunflower) seed oil | 10.0-20.0 | 12.0-14.0 | 0.3927 mL | 0.3927 mL |
| *Argania spinosa* (argan) oil | 2.0-10.0 | 5.0-7.0 | 0.18 mL | 0.18 mL |

TABLE 1A-continued

| Ingredient | Possible Range (wt. %) | Exemplary Range (wt. %) | Exemplary Formulation A | Exemplary Formulation B |
|---|---|---|---|---|
| *Borago officinalis* (borage) oil | 1.0-5.0 | 2.0-4.0 | 0.09 mL | 0.09 mL |
| *Prunus armeniaca* (apricot) kernel oil | 2.0-10.0 | 5.0-7.0 | 0.18 mL | 0.192 mL |
| Total | 100 | 100 | 3 mL | 3 mL |

A general base formula for the personal care products of the present invention based on fatty acid content is disclosed in Table 1B below.

TABLE 1B

| Ingredient | Possible Range (wt. %) Broad Range | Exemplary Range (wt. %) Preferred/Commercial Range |
|---|---|---|
| Linoleic acid in butter | 2.5-3.9 | 3.2-3.4 |
| Oleic acid in butter | 20.9-34.9 | 27.3-29.6 |
| Palmitic acid in butter | 5.3-8.9 | 7.0-7.7 |
| Stearic acid in butter | 20.4-35.7 | 27.3-29.9 |
| Linoleic acid in oil | 2.3-8.6 | 4.3-6.2 |
| Oleic acid in butter | 10.8-29.4 | 16.3-20.7 |
| Palmitic acid in butter | 0.9-3.1 | 1.6-2.2 |
| Stearic acid in butter | 0.7-2.1 | 1.1-1.5 |

Example 2

General formulas for personal care products of the present invention are disclosed in Table 2 below. Exemplary formulation C is a hand moisturizer formulation of the present invention. Exemplary formulation D is a labial moisturizer for maintaining and restoring the labial skin's natural flora and moisture.

TABLE 2

| Ingredient | Possible Range (wt. %) | Exemplary Range (wt. %) | Exemplary Formulation C | Exemplary Formulation D |
|---|---|---|---|---|
| *Theobroma cacao* (cocoa) butter | 15.0-25.0 | 20.0-22.0 | 0.627 g | 0.612 g |
| *Butyrosperum parkii* (shea nut) butter | 30.0-45.0 | 37.0-39.0 | 1.14 g | 1.14 g |
| *Garcinia indica* (kokum) seed butter | 5.0-15.0 | 9.0-11.0 | 0.3 g | 0.3 g |
| *Helianthus annuus* (sunflower) seed oil | 10.0-20.0 | 12.0-14.0 | 0.3927 mL | 0.3927 mL |
| *Argania spinosa* (argan) oil | 2.0-10.0 | 5.0-7.0 | 0.18 mL | 0.18 mL |
| *Borago officinalis* (borage) oil | 1.0-5.0 | 2.0-4.0 | 0.09 mL | 0.09 mL |
| *Prunus armeniaca* (apricot) kernel oil | 2.0-10.0 | 5.0-7.0 | 0.18 mL | 0.192 mL |
| Tocopherol (vitamin E) oil | 1.0-5.0 | 1.0-3.0 | 0.06 mL | 0.06 mL |
| Sucrose cocoate | 0.5-1.5 | 0.5-1.5 | 0.03 g | 0.03 g |
| Sodium hyaluronate | 0.005-0.015 | 0.005-0.015 | 0.0003 g | 0.0003 g |
| *Hippophae rhamnoides* (sea buckthorn) extract | 0.0-1.5 | 0.0-0.5 | — | 0.003 g |
| Total | 100 | 100 | 3 mL | 3 mL |

Example 3

General formulas for CBD containing personal care products of the present invention are disclosed below. These CBD products both moisturize the skin and provide soothing, topical relief and relaxation. Exemplary formulation E is a hand moisturizer formulation. Exemplary formulation F is a labial moisturizer for restoring the labial skin's natural flora and moisture.

TABLE 3

| Ingredient | Possible Range (wt. %) | Exemplary Range (wt. %) | Exemplary Formulation E | Exemplary formulation F |
|---|---|---|---|---|
| *Theobroma cacao* (cocoa) butter | 15.0-25.0 | 20.0-22.0 | 0.627 g | 0.612 g |
| *Butyrosperum parkii* (shea nut) butter | 30.0-45.0 | 37.0-39.0 | 1.14 g | 1.14 g |
| *Garcinia indica* (kokum) seed butter | 5.0-15.0 | 9.0-11.0 | 0.3 g | 0.3 g |
| *Helianthus annuus* (sunflower) seed oil | 10.0-20.0 | 12.0-14.0 | 0.3927 mL | 0.3927 mL |
| *Argania spinosa* (argan) oil | 2.0-10.0 | 5.0-7.0 | 0.18 mL | 0.18 mL |
| *Borago officinalis* (borage) oil | 1.0-5.0 | 2.0-4.0 | 0.09 mL | 0.09 mL |
| *Prunus armeniaca* (apricot) kernel oil | 2.0-10.0 | 5.0-7.0 | 0.18 mL | 0.192 mL |
| Tocopherol (vitamin E) oil | 1.0-5.0 | 1.0-3.0 | 0.06 mL | 0.06 mL |
| Sucrose cocoate | 0.5-1.5 | 0.5-1.5 | 0.03 g | 0.03 g |
| Sodium hyaluronate | 0.005-0.015 | 0.005-0.015 | 0.0003 g | 0.0003 g |
| *Hippophae rhamnoides* (sea buckthorn) extract | 0.0-1.5 | 0.0-0.5 | — | 0.003 g |
| Cannabidiol (CBD) oil from *cannabis sativa* (hemp) | 0.5-1.5 mg/mL | 0.5-1.5 mg/mL | 2 mg | 2 mg |
| Cannabidiol (CBD) isolate | 10.0-15.0 mg/mL | 10.0-15.0 mg/mL | 37.5 mg | 37.5 mg |
| Total | 100 | 100 | 3 mL | 3 mL |

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A personal care product, comprising
   at least about 50 wt. % of at least one plant-based glyceride butter,
   at least about 15 wt. % of at least one plant-based glyceride oil, and
   one or more of:
   vitamin E, sodium hyaluronate, sucrose cocoate, sea buckthorn powder, cannabidiol, melatonin, retinoic acid, vitamin C, collagen, glycolic acid, salicylic acid, squalene, and caffeine; and
   wherein the at least one plant-based glyceride butter comprises from about 15 wt. % to about 25 wt. % cocoa butter, from about 30 wt. % to about 45 wt. % shea nut butter, and from about 5 wt. % to about 15 wt. % kokum seed butter;
   wherein the at least one plant-based glyceride oil comprises from about 10 wt. % to about 20 wt. % high oleic sunflower seed oil, from about 2 wt. % to about 10 wt. % argan oil, and from about 1 wt. % to about 5 wt. % borage oil; and
   wherein the personal care product is in the form of a balm when stored at about 0° C. to about 5° C. for about 5 to about 10 minutes and is in the form of a serum when stored at about 36° C. to about 37° C. for about 1 to 2 minutes.

2. The personal care product of claim 1, comprising: vitamin E, and sucrose cocoate.

3. The personal care product of claim 1, comprising: vitamin E, sodium hyaluronate, sucrose cocoate and cannabidiol.

4. The personal care product of claim 1, comprising: vitamin E, sodium hyaluronate, sucrose cocoate and sea buckthorn powder.

5. The personal care product of claim 1, comprising: vitamin E, sodium hyaluronate, sucrose cocoate, sea buckthorn powder and cannabidiol.

6. The personal care product of claim 1, comprising: vitamin E, collagen, and sodium hyaluronate.

7. The personal care product of claim 1, comprising: sodium hyaluronate, sucrose cocoate, sea buckthorn powder, and cannabidiol.

8. The personal care product of claim 1, comprising: sucrose cocoate and sea buckthorn powder.

9. The personal care product of claim 1, comprising: vitamin E, sodium hyaluronate, and sucrose cocoate.

10. The personal care product of claim 1, comprising from about 50 wt. % to about 85 wt. % of the at least one plant-based glyceride butter, and from about 15 wt. % to about 45 wt. % of the at least one plant-based oil.

11. The personal care product of claim 1, wherein the at least one plant-based glyceride butter comprises:
from about 2.5 wt. % to about 3.9 wt. % linoleic acid,
from about 20.9 wt. % to about 34.9 wt. % oleic acid,
from about 5.3 wt. % to about 8.9 wt. % palmitic acid; and
from about 20.4 wt. % to about 35.7 wt. % stearic acid;
and wherein the at least one plant-based oil comprises:
from about 2.3 wt. % to about 8.6 wt. % linoleic acid,
from about 10.8 wt. % to about 29.4 wt. % oleic acid,
from about 0.9 wt. % to about 3.1 wt. % palmitic acid; and
from about 0.7 wt. % to about 2.1 wt. % stearic acid.

12. The personal care product of claim 1, wherein the personal care product is substantially free of water and alcohol.

13. The personal care product of claim 1, wherein the personal care product is substantially free of synthetic chemical, synthetic anti-microbial agent, synthetic preservative, or a synthetic hormone.

14. The personal care product of claim 1, wherein the personal care product has a pH of from about 3.7 to about 6.5 in an aqueous environment.

15. The personal care product of claim 1, wherein the at least one plant-based glyceride oil further comprises from about 2 wt. % to about 10 wt. % apricot kernel oil.

16. The personal car product of claim 15, comprising vitamin E, sodium hyaluronate, sucrose cocoate and cannabidiol.

17. The personal car product of claim 15, comprising vitamin E, sodium hyaluronate, sucrose cocoate and sea buckthorn powder.

18. The personal car product of claim 15, comprising vitamin E, sodium hyaluronate, sucrose cocoate, sea buckthorn powder and cannabidiol.

19. The personal car product of claim 15, comprising vitamin E, sodium hyaluronate, and sucrose cocoate.

20. A method for maintaining and restoring skin's natural flora and moisturizing skin of a subject in need thereof, said method comprising applying onto the skin of said subject an effective amount of the personal care product of claim 1.

21. The method of claim 20, wherein the personal care product is effective for retaining moisture and natural flora in the vaginal lips or the hands.

* * * * *